United States Patent [19]
Joseph et al.

[11] Patent Number: 5,301,541
[45] Date of Patent: Apr. 12, 1994

[54] DRAG DETERMINING APPARATUS

[76] Inventors: Daniel D. Joseph, 1920 S. First St., Apt. 2302, Minneapolis, Minn. 55454; Francis J. Marentic, 7880 Pinehurst Rd., Woodbury, Minn. 55125; Clement A. Nelson, 24 N. Oaks Rd., St. Paul, Minn. 55127

[21] Appl. No.: 901,493

[22] Filed: Jun. 19, 1992

[51] Int. Cl.⁵ .......................................... G01N 11/02
[52] U.S. Cl. .................................... 73/54.32; 73/54.28
[58] Field of Search ................. 73/54.28, 54.32, 54.39, 73/54.01, 54.23, 54.35

[56] References Cited

U.S. PATENT DOCUMENTS

| | | | |
|---|---|---|---|
| 2,398,574 | 4/1946 | Bell | 73/54.28 |
| 2,484,761 | 10/1949 | Stock | 73/54.33 |
| 2,817,231 | 12/1957 | Barstow | 73/54.33 |
| 2,977,790 | 4/1961 | Dubsky et al. | 73/54.33 |
| 2,992,651 | 7/1961 | Krofta | 73/54.33 |
| 3,122,914 | 3/1964 | Stabe et al. | 73/54.38 |
| 3,292,423 | 12/1966 | Banks | 73/54.28 |
| 4,045,999 | 9/1977 | Palmer | 73/54.35 |
| 4,062,225 | 12/1977 | Murphy, Jr. et al. | 73/54.35 |
| 4,077,251 | 3/1978 | Winter | 73/54.39 |
| 4,175,425 | 11/1979 | Brookfield | 73/54.28 |
| 4,347,734 | 9/1982 | Heinz | 73/54.33 |
| 4,485,450 | 11/1984 | Characklis et al. | 364/550 |
| 4,566,324 | 1/1986 | Vinogradov et al. | 73/54.39 |
| 4,570,478 | 2/1986 | Soong | 73/54.39 |
| 4,630,468 | 12/1986 | Sweet | 73/54.32 |
| 4,648,263 | 3/1987 | Deysarkar et al. | 73/54.35 |
| 4,765,180 | 8/1988 | Clifton | 73/54.33 |
| 4,878,378 | 11/1989 | Harada | 73/54.39 |
| 5,042,292 | 8/1991 | Plint et al. | 73/54.39 |
| 5,167,143 | 12/1992 | Brookfield | 73/54.39 |

Primary Examiner—James C. Housel
Assistant Examiner—Theresa A. Trembley
Attorney, Agent, or Firm—Westman, Champlin & Kelly

[57] ABSTRACT

An apparatus and method for determining the effect of the configuration of an outer surface of an object on the drag of the object. The apparatus comprises a housing, an inner block suspended in the housing, a motor for rotating the housing, and a torquemeter. The inner block is connected to the torquemeter by a suspending rod and universal joint. The method comprises attaching a layer of material having a desired surface configuration to the inner block and to the housing, filling the housing with a fluid, and driving the motor so that the housing is rotated. The magnitude of the torque on the inner block is then measured by the torquemeter. The rate of rotation of the housing and the temperature of the water are monitored.

17 Claims, 3 Drawing Sheets

DRAG DETERMINING APPARATUS

BACKGROUND OF THE INVENTION

The present invention relates to an apparatus for determining the effect of the configuration or topography of an outer surface on the drag of an object in a fluid and, in particular, to an apparatus and method used to determine the effect of surfaces having riblets and other small surface irregularities on the drag of an object in couette flow.

A reduction in the drag caused by the outer surface of an object can affect both the speed and direction of an object moving through a fluid. More specifically, the drag reducing effects of the outer surface of an object moving through a fluid, or the inner surface of an object through which a fluid moves, can be significant. Such drag reducing effects can have practical applications ranging from more efficient fluid flow in pipes to improving the performance of racing yachts.

A surface of parallel, elongated riblets has been shown to produce drag reductions in pipes and on flat plates, when the riblets meet certain specifications. It is desired to determine whether a riblet surface also reduces the drag of an object in couette flow, and to compare the results of different riblet profiler and other surface topographies.

To determine the extent to which riblet and other surfaces can reduce the drag of an object in couette flow, a method and testing apparatus is needed. The method and testing apparatus must enable the accurate comparison of the drag reduction of each surface tested.

SUMMARY OF THE INVENTION

The present invention provides an apparatus and method for determining the effect of the configuration of an outer surface on the drag of an object in a fluid moving relative to the object. The apparatus comprises a housing having a fluid filled chamber, a block, a torquemeter and a variable speed motor for moving the housing and the block relative to each other. The block supports a layer of material having an outer surface configuration to be tested.

The housing has a containment wall, a base wall covering a first end of the containment wall and a containment cap removably attached to a second end of the containment wall. A drive shaft extends from a motor and is attached to the base wall so that the motor can rotate the housing.

The block is suspended inside the housing by a suspending rod which extends from a first end of the block through an opening in the containment cap. The suspending rod is connected to the torquemeter through a universal joint.

The method of the present invention first involves attaching a layer of material having the test surface applied as shown to the block and the inner surface of the containment wall. A space between the block and the containment wall is then filled with a fluid, which is usually a liquid such as water. The motor is then driven so that the drive shaft rotates the housing, moving the containment wall relative to the block.

When the housing rotates, the water will exert a drag on the block creating a torque on the block. The magnitude of this torque is measured by the torquemeter. During operation, a sensor measures the rate of rotation of the housing and a temperature probe may be used to monitor the temperature of the water.

If desired, the block can be rotated instead of the housing. In addition, various spacings between the housing and the block may be utilized for liquids having different viscosities.

DETAILED DESCRIPTION OF THE PREFERRED EMBODIMENTS

Figure 1:
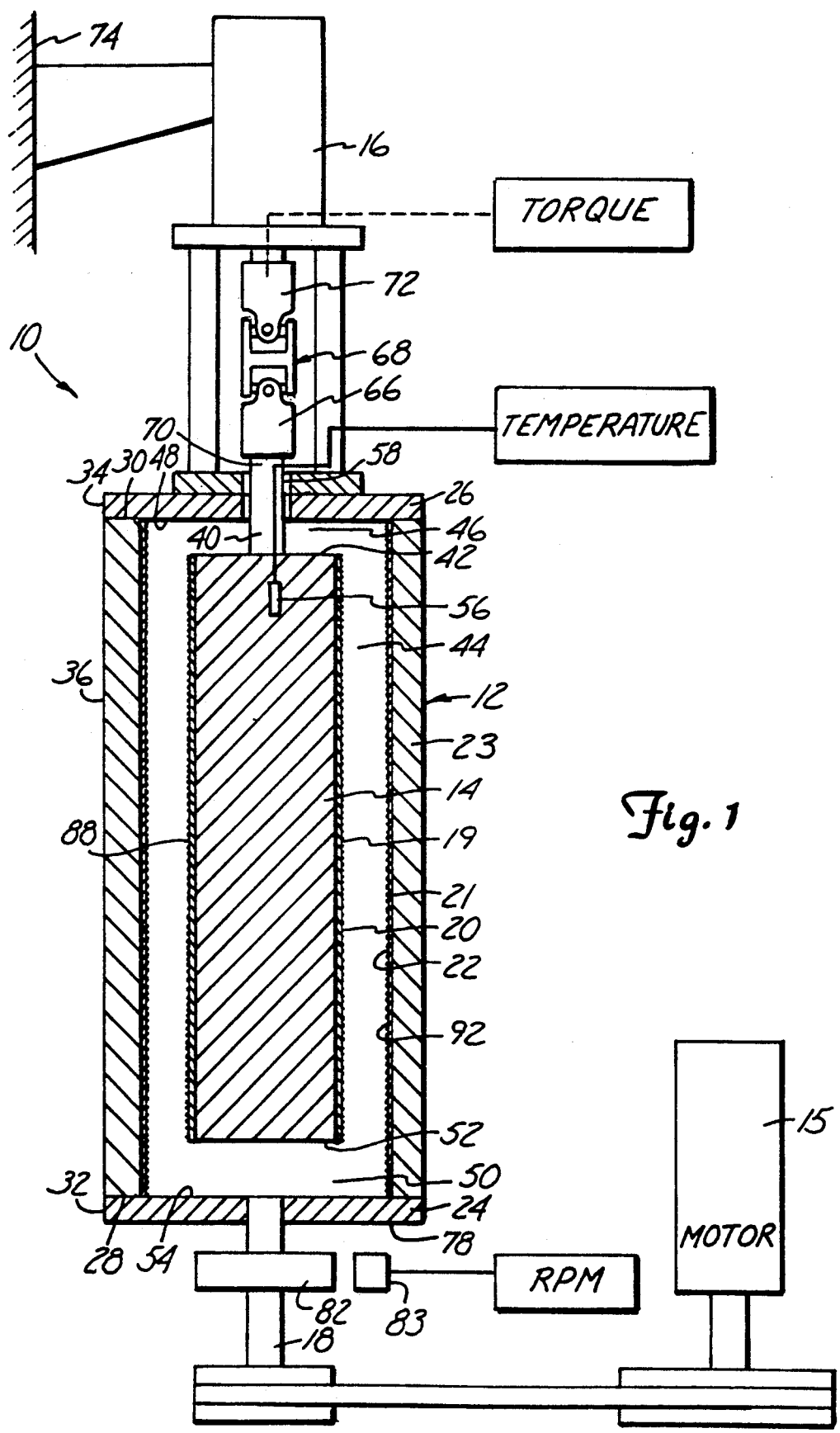
FIG. 1 is a schematic representation of the apparatus of the present invention.

A schematic representation of the drag determining apparatus 10 of the present invention is shown in FIG. 1. The apparatus 10 comprises a housing 12, an inner block or support 14 suspended inside the housing 12, a variable speed motor 15 for rotating the housing 12 and a torquemeter 16 supporting and restraining rotation of the inner block 14. A drive shaft 18 extends from the motor 15 and is connected to the housing 12. A first layer of material 19 having a surface 20 with a riblet configuration is attached to the inner block 14 and a second layer of material 21 having a surface 22 with a riblet configuration is attached to the inner surface of the housing 12.

Figure 2:
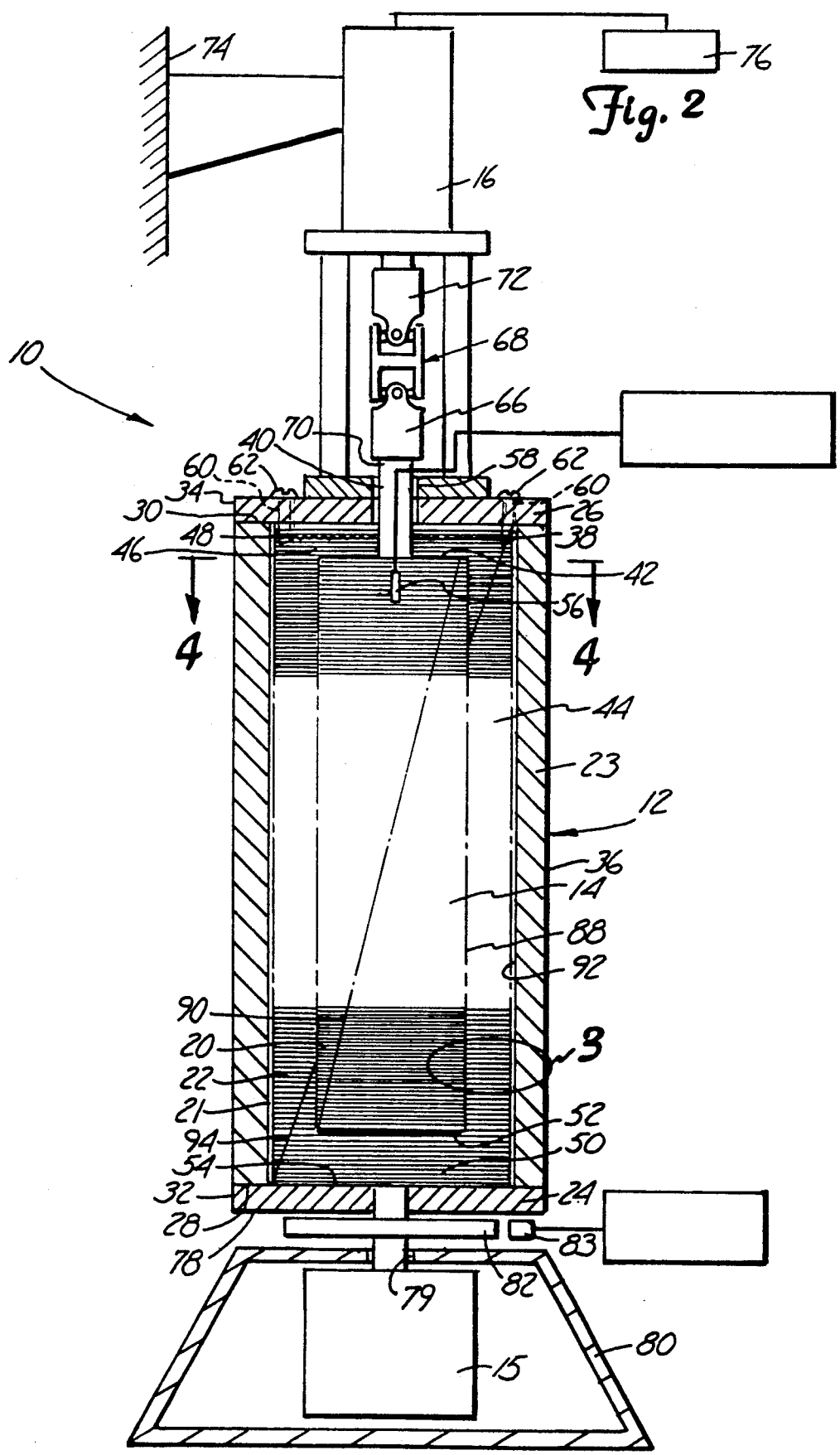
FIG. 2 is a sectional view of a housing of the apparatus of the present invention showing a surface of an inner block.

The housing 12 is shown in more detail in FIG. 2 and has the general shape of a hollow cylinder having a cylindrical containment wall 23 and a disc-shaped base wall 24. A removable disc-shaped containment cap 26 covers an upper end of the housing 12. The base wall 24 is integral with a first end 28 of the containment wall 23 so as to form a Watertight seal while the containment cap 26 is attached to a second end 30 of the containment wall 23. The containment wall 23 has the same diameter as both the base wall 24 and the containment cap 26 so that both a base wall outer edge 32 and a containment cap outer edge 34 are flush with an outer surface 36 of the containment wall 23. The housing 12 is filled with a fluid such as water to a level 38.

Figure 4:
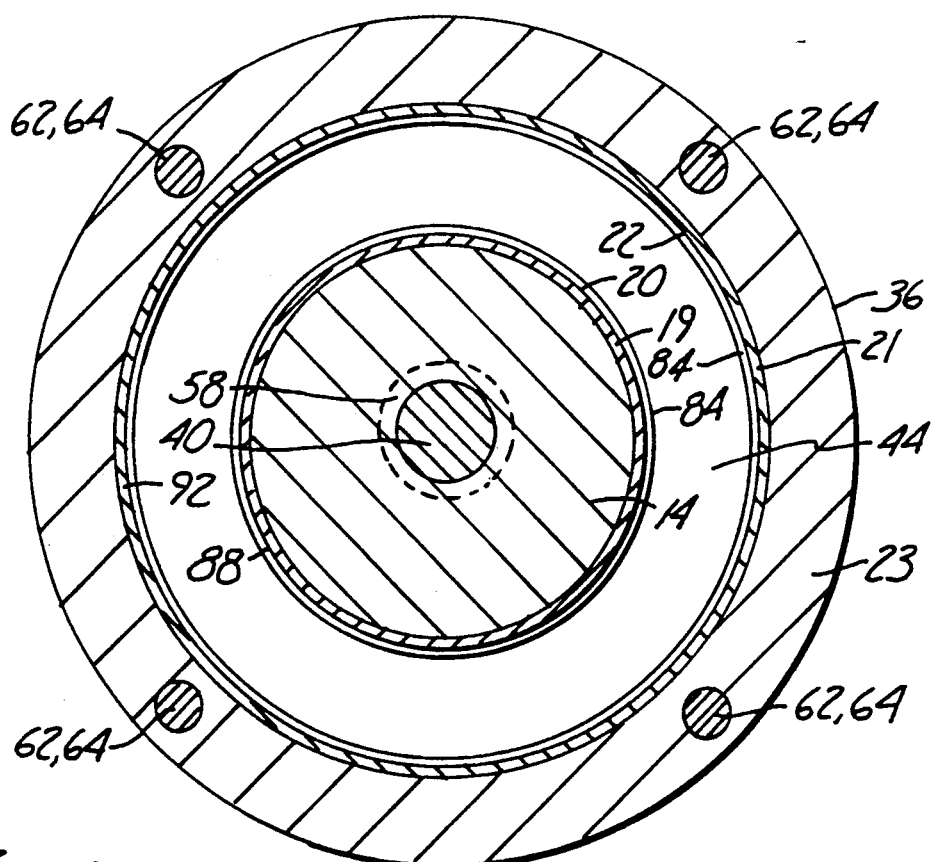
FIG. 4 is a sectional view of the apparatus of the present invention taken along the line 4—4 of FIG. 2.

The inner block 14 has a generally cylindrical shape and is suspended inside the housing 12 by a suspending rod 40 which extends from the center of a first end 42 of the inner block 14. The inner block 14 is concentric with the containment wall 23 so as to form an annular space 44, shown in FIG. 4, between the inner block 14 and the containment wall 23. A first end space 46 separates the first end 42 of the inner block 14 and a facing surface 48 of the containment cap 26. A second end space 50 separates a second end 52 of the inner block 14 and a facing surface 54 of the base wall 24. A temperature probe 56 is shown mounted on the inner block 14 to measure the temperature of the water contained in the housing 12.

The containment cap 26 has a circular opening 58 at its center through which the suspending rod 40 is inserted such that the suspending rod 40 does not come into contact with the containment cap 26. The containment cap 26 has four holes 60 equally spaced around the cap 26. A screw 62 is inserted through each hole 60 and into a corresponding one of four threaded holes 64 in the second end 30 of the containment wall 23. The containment cap 26 is thus attached to the second end 30 of the containment wall 23 so as to form a watertight seal.

A first half 66 of a self-centering universal joint 68 is attached to an end 70 of the suspending rod 40 furthest from the inner block 14 while a second half 72 of the universal joint 68 is connected to the torquemeter 16. Any torque exerted on the inner block 14 is transmitted through the suspending rod 40 and the universal joint 6B to the torquemeter 16. The torquemeter 16, which is anchored to a side support 74, measures the magnitude of the torque and sends the measurement to a recording device 76. The measurement can also be sent to a visual display, processing circuit, or other known devices.

The drive shaft 18 extends from the motor 15, through a circular opening 79 in a motor housing 80, and is attached to the center of the base wall 24. The drive shaft 18 is rotated by the motor 15 when the motor 15 is running. The drive shaft 18, when rotated by the motor 15, will rotate the base wall 24 and therefore the housing 12. A disc 82 having a magnet at its periphery is mounted on the drive shaft 18 and a sensor 83 senses each passage of the magnet to monitor the speed of the drive shaft 18, which is the same as that of the housing 12. The drive shaft 18 can also be connected to the motor 15 through the use of belts, gears and other known drives.

Figure 3:
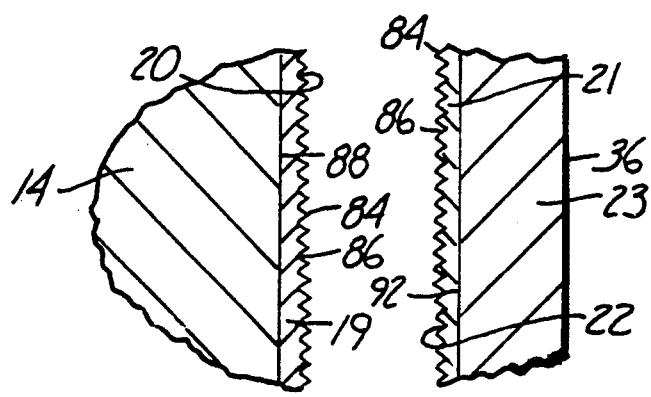
FIG. 3 is an enlarged sectional view of a portion of the apparatus of the present invention which is circled in FIG. 2.

The first layer of material 19 and the second layer of material 21 are shown in detail in FIG. 3. The surfaces 20,22 as shown comprise a series of parallel, elongated riblets 84 that form shallow triangular grooves 86 between them. Although layers of material having a riblet surface configuration are shown, layers having other surface configurations or topographies can be used.

The first layer of material 19 has the general peripheral shape of a parallelogram and is of size to cover a cylindrical surface 88 of the inner block 14 without overlap of the ends of the first layer 19. The first layer 19 is attached or adhered to the inner block 14 so that the riblets 84 encircle the inner block 14 and each riblet 84 lies on a plane perpendicular to the longitudinal axis of the inner block 14. A first seam 90 is formed where the ends of the first layer 19 meet and extends diagonally along the cylindrical surface 88 of the inner block 14.

The second layer of material 21 has the same peripheral shape as the first layer 19 and is of size to cover an inner surface 92 of the containment wall 23. The material layer 21 is attached or adhered to the containment wall 23 so that the riblets 84 encircle the containment wall 23 and each riblet 84 lies on a plane perpendicular to the longitudinal axis of the containment wall 23. A second seam 94 is formed where the ends of the second layer 21 meet and extends diagonally along the inner surface 92 of the containment wall 23 in a spiral direction opposite that of the first seam 90. Both the first layer 19 and the second layer 21 are attached using a suitable adhesive.

In operation, the first layer of material 19 is attached to the cylindrical surface 88 of the inner block 14. The first layer 19 is positioned such that the opposite ends of each riblet 84 on surface 20 are aligned and the first seam 90 extends diagonally from the first end 42 of the inner block 14 to the second end 52 of the inner block 14. The second layer 21 is then attached to the inner surface 92 of the containment wall 23 such that the opposite ends of each riblet 84 on surface 22 are aligned and the second seam 94 extends diagonally from the first end 28 of the containment wall 23 to the second end 30 of the containment wall 23.

The housing 12 is filled with water until the annular space 44 between the inner block 14 and the containment wall 23 is completely filled. The motor 15 is then driven at a desired speed and rotates the drive shaft 18 which rotates the housing 12. The second layer of material 21 is thus put in motion with respect to the first layer of material 19.

The rotation of the housing 12 creates a couette flow in the water. This movement of the water exerts a drag force on the inner block 14 and creates a measurable torque tending to rotate the inner block 14 which is transmitted through the suspending rod 40 and the universal joint 68 to the torquemeter 16. The magnitude of this torque is then measured by the torquemeter 16. The diagonal orientations of the first seam 90 and the second seam 94 prevent them from causing an aberration in the magnitude of the torque each time the second seam 94 passes the first seam 90.

The drag reducing effect of the surfaces 20,22 is determined by comparing the magnitude of the torque exerted on the inner block 14 with the torque exerted on the inner block 14 when layers of material having surfaces with smooth configurations are attached to the inner block 14 and the containment wall 23. The layers having smooth surface configurations are made of the same material, have the same shape and are attached in the same manner as the first layer 19 and the second layer 21 to assure that all conditions, other than the surface configurations, are equal. The same method can be used to determine the effect on drag of other surface configurations.

The first layer of material 19 and the second layer of material 21 may be fabricated from a variety of materials including synthetic materials made by 3M Company. These and other materials may absorb water, as may the housing 12, so that they expand when in water. Therefore it may be necessary to preconditioned the housing 12, as well as the first and second layers 19,21, in water when not in use that is, prior to testing. Testing of material having a variety of surface configurations, such as the riblets, sharkskin, and other materials may be used in the drag determining apparatus 10.

The method of the present invention can be performed where one layer of material, attached to either the inner block 14 or the containment wall 23, has a smooth surface configuration. The other layer of material would then have a surface configuration to be tested. In addition, the present invention can be designed so that the inner block 14 is rotated instead of the housing 12 to put the first layer of material 19 in motion with respect to the second layer of material 21.

Finally, although the opposite ends of each riblet 84 are described as being aligned, it is possible for the ends to be slightly out of alignment so that the riblets 84 are at a slight angle to the flow of water.

Although the present invention has been described with reference to preferred embodiments, workers skilled in the art will recognize that changes may be made in form and detail without departing from the spirit and scope of the invention.

What is claimed is:

1. A method used to determine the effect of the surface configuration of an outer surface of an object on the drag of the object in a fluid, the method comprising the steps of:

provide a housing having a chamber and a block in the chamber spaced from walls of the chamber;

filling a space between an inner surface of the housing and an outer surface of the block with a fluid;

providing a layer of material having a desired surface configuration on at least one of the inner surface of the housing and the outer surface of the block;

rotating one of the housing and the block while the other of the housing and the block remains substantially stationary so that the inner surface of the housing moves relative to the outer surface of the block; and measuring the magnitude of the torque exerted on the stationary one of the housing and the block during the rotation step.

2. The method according to claim 1 including the step of comparing the magnitude of the torque measured when at least one of the layers of material provided has a different surface configuration from the desired surface configuration.

3. The method according to claim 1 including the step of providing a torquemeter for measuring the magnitude of the torque in the measuring step.

4. The method according to claim 1 including the step of providing a sensor for measuring the rate of rotation of the one of the housing and the block that is rotated during the rotating step.

5. The method according to claim 1 including the step of providing a temperature probe for monitoring the temperature of the fluid during the rotating step.

6. An apparatus for determining the effect of a layer of material having a desired surface configuration and attached to a surface of an object on the drag of the object in a fluid, the apparatus comprising:

a housing having a wall forming a housing chamber, wherein an inner surface of the housing is capable of having a layer of material attached thereto;

a block in the housing chamber spaced from the wall of the housing so that there is a space between the inner surface of the housing and a facing outer surface of the block, wherein the outer surface of the block is capable of having a layer of material attached thereto;

a fluid filling the space between the wall of the housing and the block;

rotating means for rotating one of the housing and the block so that the inner surface of the housing is put in motion relative to the outer surface of the block;

torque measuring means for measuring the magnitude of torque exerted on the one of the housing and the block that is not rotated by the rotating means; and a layer of material having a desired surface configuration removable attached to at least one of the outer surface of the block and the inner surface of the housing.

7. The apparatus according to claim 6 wherein the layer of material has a surface configuration comprising a series of parallel, elongated riblets.

8. The apparatus according to claim 6 wherein the space between the inner surface of the housing and the outer surface of the block is filled with the fluid.

9. The apparatus according to claim 8 wherein a temperature probe is used to monitor the temperature of the fluid.

10. The apparatus according to claim 6 wherein the block is suspended int he housing chamber by a suspending rod which extends through an opening in an upper end of the housing.

11. The apparatus according to claim 6 wherein the block has the general shape of a cylinder.

12. The apparatus according to claim 11 wherein the housing has the general shape of a hollow cylinder and is concentric with the block.

13. The apparatus according to claim 6 wherein the rotating means comprises a motor having a drive shaft.

14. The apparatus according to claim 13 wherein a first end of the drive shaft is attached to a lower end of the housing.

15. The apparatus according to claim 13 wherein a first end of the drive shaft is attached to an upper end of the block.

16. The apparatus according to claim 6 wherein the torque measuring means comprises a torquemeter connected to the one of the housing and the block that is not being rotated.

17. The apparatus according to claim 6 wherein a rotation sensor is used to monitor the rate of rotation of the one of the housing and the block that is being rotated.

* * * * *

UNITED STATES PATENT AND TRADEMARK OFFICE
CERTIFICATE OF CORRECTION

PATENT NO. : 5,301,541
DATED : April 12, 1994
INVENTOR(S) : Daniel D. Joseph et al.

It is certified that error appears in the above-indentified patent and that said Letters Patent is hereby corrected as shown below:

```
Column 6, line 10, cancel "removable" and
    insert --removably--.

Column 6, line 23, cancel "int he" and insert --in the--.
```

Signed and Sealed this

Sixteenth Day of August, 1994

Attest:

BRUCE LEHMAN

*Attesting Officer*    *Commissioner of Patents and Trademarks*